US008586064B2

(12) United States Patent
Meakin et al.

(10) Patent No.: US 8,586,064 B2
(45) Date of Patent: Nov. 19, 2013

(54) TREATING ECZEMA AND/OR PSORIASIS

(71) Applicant: Lypanosys Pte Limited, Singapore (SG)

(72) Inventors: Timothy David Meakin, Auckland (NZ); Dianne Cadwallader, Auckland (NZ); Craig Leonard Heatley, Auckland (NZ)

(73) Assignee: Lypanosys Pte Limited, Singapore (SG)

( * ) Notice: Subject to any disclaimer, the term of this patent is extended or adjusted under 35 U.S.C. 154(b) by 0 days.

(21) Appl. No.: 13/753,279

(22) Filed: Jan. 29, 2013

(65) Prior Publication Data

US 2013/0237600 A1 Sep. 12, 2013

Related U.S. Application Data

(60) Continuation of application No. 13/405,203, filed on Feb. 24, 2012, which is a continuation of application No. 11/056,008, filed on Feb. 14, 2005, now Pat. No. 8,147,851, which is a division of application No. 10/275,269, filed as application No. PCT/NZ01/00085 on May 11, 2001, now abandoned.

(30) Foreign Application Priority Data

May 12, 2000 (NZ) ........................ 504525
Sep. 28, 2000 (NZ) ........................ 507228

(51) Int. Cl.
*A61K 9/00* (2006.01)

(52) U.S. Cl.
USPC .......................... 424/400; 514/546

(58) Field of Classification Search
None
See application file for complete search history.

(56) References Cited

U.S. PATENT DOCUMENTS

| | | | |
|---|---|---|---|
| 3,169,099 A | 2/1965 | Davis | |
| 4,049,824 A | 9/1977 | Diehl | |
| 4,113,881 A | 9/1978 | Diehl | |
| 4,518,614 A * | 5/1985 | Parkinson | 514/18.8 |
| 4,642,233 A | 2/1987 | Urquhart et al. | |
| 4,851,231 A | 7/1989 | Urquhart et al. | |
| 5,399,360 A | 3/1995 | Surer et al. | |
| 5,436,230 A | 7/1995 | Soudant et al. | |
| 5,496,565 A | 3/1996 | Heinze et al. | |
| 5,569,676 A | 10/1996 | Diehl | |
| 5,863,546 A * | 1/1999 | Swinehart | 424/401 |
| 5,886,038 A | 3/1999 | Glenn et al. | |
| 6,417,227 B1 | 7/2002 | Lord et al. | |
| 6,485,950 B1 | 11/2002 | Kumar et al. | |
| 6,677,321 B1 | 1/2004 | Levin | |
| 6,696,491 B2 | 2/2004 | Meakin et al. | |
| 7,411,079 B2 | 8/2008 | Cadwallader et al. | |
| 2002/0147208 A1 | 10/2002 | Fleshner-Barak et al. | |
| 2005/0004216 A1 | 1/2005 | Cadwallader et al. | |
| 2007/0020254 A1 | 1/2007 | Levin | |
| 2007/0225368 A1 | 9/2007 | Cadwallader et al. | |

FOREIGN PATENT DOCUMENTS

| | | |
|---|---|---|
| AU | 2001260833 B2 | 9/2005 |
| CA | 2408541 C | 11/2001 |
| EP | 1335719 B1 | 8/2003 |
| GB | 2170407 A | 8/1986 |
| GB | 2337461 B | 11/1999 |
| WO | WO-99/52508 | 10/1999 |
| WO | WO-99/56733 A1 | 11/1999 |
| WO | WO-99/60167 A1 | 11/1999 |
| WO | WO-00/07627 A2 | 2/2000 |
| WO | WO-00/64436 A1 | 11/2000 |
| WO | WO-00/67728 A2 | 11/2000 |
| WO | WO-01/08162 A1 | 2/2001 |
| WO | WO-01/85162 | 11/2001 |
| WO | WO-01/85164 A1 | 11/2001 |
| WO | WO-03/018731 A1 | 3/2003 |
| WO | WO-03/026640 A1 | 4/2003 |
| WO | WO-03/045374 A1 | 6/2003 |
| WO | WO-2005/118070 A1 | 12/2005 |

OTHER PUBLICATIONS

Amerex Corp., "Questions about Cetyl Myristate," Internet Publication XP002265348, Jan. 20, 1999.
Amerex Corp., "What is cetyl myristate," Internet Publication XP002265364, Jan. 20, 1999.
Austin et al. Hay fever, eczema, and wheeze: a national UK study (ISAAC, international study of asthma and allergies in childhood), Arch, Dis. Child., 1999, vol. 81, pp. 225-230.
Boguniewicz et al. (1998). J Allergy Clin Immunol 102:637-44.
Brehler et al. (1997). J Am Acad Dermatol 36:983-94.
Cetyl Esters: Bindu Bair, the Cosmetic Ingredient Review Expert Panel, (international Journal of Toxicology), Suppl. 1:123-130, 1997.
Correale et al. (1999). Am Fam Physician 60:1191-210.
Dermatitis_Merck Manual Home Edition#sec1.pdf.
Drake et al. (1994). J Am Acad Dermatol 31:613-6.
Eldred et al. Treatment of Acute atopic eczema by Chiropractic care, A case study, vol. 8, No. 3, Nov. 1999).
Halbert et al. (1995). J Am Acad Dermatol 33:1008-18.
Holgate and Finnerty (1989). J Allergy Clin Immunol 83:537-47.
International Search Report mailed Jul. 26, 2001, for PCT/NZ2001/000086 filed May 11, 2001, 2 pages.
Johansson et al. (2001). Allergy 56:813-24.
Krause and Shuster (1983). BMJ 287:1199-1200.
Mallet and Henocq (1992). J Pediatr 121:S95-S100.
McHenry et al. (1995). BMJ 310:843-47.
Moffatt et al. (Genetics of asthma and inflammation: the status, current opinion in immunology 1999, 11:606-606).
Rothe and Grant-Kels (1996). J Am Acad Dermatol 35:1-13.
Sears et al. (1990). Lancet 336:1391-96.
Whole Health Discount Center, "Myristin," Internet Publication XP002265368, Dec. 16, 2003.

\* cited by examiner

*Primary Examiner* — Brandon Fetterolf
*Assistant Examiner* — Jean Cornet
(74) *Attorney, Agent, or Firm* — Morrison & Foerster LLP

(57) ABSTRACT

The treatment of humans or other mammals for eczema and/or psoriasis using dosage forms or compositions that include cetyl myristate alone or (in admixture or serially) both cetyl myristate and cetyl palmitate.

8 Claims, No Drawings

TREATING ECZEMA AND/OR PSORIASIS

CROSS REFERENCE TO RELATED APPLICATIONS

This application is a continuation of U.S. application Ser. No. 13/405,203, filed Feb. 24, 2012, which is a continuation of U.S. application Ser. No. 11/056,008, filed Feb. 14, 2005, now U.S. Pat. No. 8,147,851, which is a divisional of U.S. application Ser. No. 10/275,269, filed Feb. 12, 2003, now abandoned, which is a national phase of PCT Application No. PCT/NZ01/00085, filed May 11, 2001, which claims benefit of New Zealand Application No. 507228, filed Sep. 28, 2000 and New Zealand Application No. 504525, filed May 12, 2000, which are incorporated herein by reference in their entirety.

TECHNICAL FIELD

The present invention relates to a method of treatment and/or prophylaxis of eczema and psoriasis.

BACKGROUND

Eczema can be described as an inflammation of the skin where swelling, redness, itching or a burning sensation is present. Sometimes the first inflammation is felt, rather than seen, as it is immediately beneath the skin's surface. Eczema can also be seen as reddened spots, scales, crusts or blisters may also be present, either alone or in combination. It may take a mild form, or be more severe, as in the case of psoriasis.

The present invention has surprisingly determined that the ingestion of cetyl myristate, and particularly cetyl myristate in conjunction with cetyl palmitate, provides an effective treatment of eczema and/or psoriasis.

Cetyl myristate and cetyl palmitate can each be sourced from animals or vegetables. Cetyl myristate is not to be mistaken for cetyl myristoleate which is also a fatty acid derived traditionally from spermaceti by saponification and more recently from the tallow of bovine(s).

Reference is made to U.S. Pat. No. 4,113,881 where it is disclosed that the administration of an effective amount of cetyl myristoleate to a mammal is useful in inhibiting or relieving the symptoms of inflammatory rheumatoid arthritis in mammals. Also in U.S. Pat. No. 5,569,676 there is disclosure of the use of cetyl myristoleate in the treatment of osteoarthritis.

It is thought that cetyl myristate has a negligible anti-arthritic activity in laboratory experiments and reference is made to the website www.gcinutrients.com/Newletter.com. However this point is arguable and a product known as cetyl myristate sold by Amerex Corporation of Vista, Calif. purports that cetyl myristate is useful for the treatment of arthritis.

Cetyl myristate is derived from the saturated fatty acid, myristic acid. This acid is found in nutmeg butter, in the fats of Myristicaceae, in palm seed fats, milk fats and also sperm whale oil. Reference is made to U.S. Pat. No. 2,481,365 which discloses the preparation of myristic acid from tall-oil fatty acids. It is to be noted that Amerex Corporation source the cetyl myristate used in their products from sunflower oil. See their website at www.hollinet.com.

Cetyl palmitate is derived from the fatty acid, palmitic acid which occurs as the glycerol ester in many oils and fats such as palm oil or Chinese vegetable tallow. A synthetic method of preparation is to react palmitoyl chloride and cetyl alcohol in the presence of magnesium. See the Merck Index, 12th edition at page 336. Reference is also made to U.S. Pat. No. 3,169,099 which discloses a biosynthetic method of producing cetyl palmitate.

It is an objection of the present invention to provide a medicament to aid in the treatment and/or prophylaxis of eczema and psoriasis which will provide an alternative to existing treatments or to provide the public with a useful choice.

DISCLOSURE OF INVENTION

As indicated earlier the present invention is directed to the treatment and/or prophylaxis of eczema and/or psoriasis reliant upon administration (whether by self administration or otherwise) of either cetyl myristate or cetyl myristate and cetyl palmitate (whether given simultaneously in admixture or not or given serially).

The present invention also encompasses the prospect of dosage forms that in some instances might contain cetyl myristate alone and in other instances both cetyl myristate and cetyl palmitate and dosage regimes that might use one dosage form or both.

In another aspect the invention is a method of treatment and/or prophylaxis of a mammal for eczema and/or psoriasis which comprises or includes administering or having self administered to such mammal an effective amount of either
  (a) cetyl myristate, or
  (b) cetyl myristate and cetyl palmitate.

Preferably said administration is orally of (b) whether as a mixture of both cetyl myristate and cetyl palmitate, or serially.

Preferably the effective amount is of (b).

Preferably said administration is with a mixture of cetyl myristate in conjunction with cetyl palmitate where the cetyl myristate comprises from 50 to 98% w/w of the mixture.

Preferably said effective amount of (a) or (b) is by means of one or more capsules.

In one type of use said mammal is a human being suffering from eczema and the administration is for treatment purposes.

In another type of use said mammal is a human being suffering from psoriasis and the administration is for treatment purposes.

In another aspect the invention is an oral pharmaceutical composition for treating eczema which comprises or includes both cetyl myristate and cetyl palmitate.

In still another aspect the invention is an oral pharmaceutical composition for treating psoriasis which comprises or includes both cetyl myristate and cetyl palmitate.

Preferably said cetyl myristate comprises at least 50% by weight of the composition.

Preferably said composition also includes at least one pharmaceutically acceptable excipient and/or diluent.

In still another aspect the invention is an oral dosage unit effective in the treatment of eczema and/or psoriasis, said dosage unit having either
  (a) cetyl myristate, or
  (b) a mixture of cetyl myristate and cetyl palmitate.

Preferably said dosage unit has (b) and said cetyl myristate in any such mixture comprises from 50 to 98% w/w of the mixture.

In another variant the dosage unit has (a) only and there is between 5 to 400 mg of cetyl myristate.

Preferably in the dosage use, where (b) is present, there is from 5 to 400 mg of the mixture of cetyl myristate and cetyl palmitate.

Preferably (a) or (b) is in a capsule.

Preferably said capsule also includes a pharmaceutically acceptable excipient and/or diluent.

Preferably the dosage unit includes silicon dioxide.

Preferably the dosage unit also contains calcium phosphate and/or magnesium oxide.

Preferably the dosage unit also includes additionally at one trace element.

In another aspect the invention is a liquid composition being also a composition as aforesaid or a dosage unit as aforesaid.

In another aspect the invention is the use, in the manufacture of oral dosage units for the treatment or prophylaxis of eczema and/or psoriasis in a mammal, of (a) cetyl myristate, or
(b) a mixture of cetyl myristate and cetyl palmitate, or
(c) cetyl palmitate.

In another aspect the invention is the use, in the manufacture of oral dosage units for the treatment or prophylaxis of eczema and/or psoriasis in a mammal, of (i) cetyl myristate, and
(ii) cetyl palmitate.

We have also noted that the present invention in conjunction with an accelerated wound healing utilising topical composition (for example as disclosed in U.S. Pat. No. 4,775,291) can supplement effectively the effects thereof with oral dosages of either (a) or (b) as defined above.

The mixture can use cetyl myristate available from a commercial source such as EHP Products Inc., Mt. Pleasant, S.C. or Amerex Corporation, Vista, Calif.

The mixture can use cetyl palmitate derived from a source such as, for example, Quimica Croda, S.A. de C.V, Circuito Medicos No. 47. Apdo. Postal 71-A Cd. Satelite, 53100 Naucalpan, Edo. de Mexico, Mexico or online at www.butterburandsage.com.

Most ideally however the mixture is synthesized from starting materials utilising the procedures as disclosed in New Zealand Patent Specification No. 332959 which involves reacting both myristic acid and palmitic acid with a cetyl alcohol at an elevated temperature in the presence of at least one acid catalyst and at least one aromatic hydrocarbon. The aromatic hydrocarbon fraction then contains the cetyl myristate and cetyl palmitate from whence it can be crystallised.

The full content of NZ 332959 is here incorporated by way of reference.

This crystallised form can then be ground up, dissolved and mixed with a suitable general pharmacy liquid to be administered to a person. The crystals are usually dissolved in hot water before adding to the pharmacy liquid which is usually a sugar syrup available from most pharmaceutical companies. The liquid is made up to a concentration of 70 w/v.

Alternatively the crystals may be ground up into a powder and combined with magnesium oxide, silicon oxide and fine di-calcium phosphate. This powder can then be transferred into capsules for oral ingestion into the body. The capsules used are VEGICAP™ that are non-gelatin containing.

The mode of administration is preferably oral. The dosage unit can be either a swallowable capsule or some alternative (preferably having the active ingredient(s) as a wax-like solid or can be an orally consumable liquid composition (e.g., made up with a general pharmacy type carrier such as methyl cellulose)).

Other modes of administration can include transdermal and suppository delivery (the latter being generally contraindicated having regard to the targeted condition).

The administration process involves either orally ingesting capsules or drinking the liquid formulation either on an empty stomach or not. The number of capsules or liquid taken depends on the size and severity of the persons condition. Generally, an adult suffering from Eczema and/or psoriasis is advised to take at least 4 capsules 3 times daily of a dosage unit as described in the invention, whereas for a child this is reduced to half or less. The dosage may be increased or decreased depending on whether the symptoms begin to clear up.

Similarly for the liquid formulation where an amount of liquid equivalent to at least 4 capsules is prescribed which is to be taken 3 times daily. That is 4200 mg of cetyl myristate or the mixture of cetyl myristate and cetyl palmitate.

The present invention will hereafter be described with reference to trial examples which give an indication of the condition of the patient prior to taking the dosage unit of either the capsule or liquid form as described in the present invention and the subsequent condition of the patient after taking the dosage unit as described in the present invention.

The condition of a flexural point of patient 1 before taking the liquid dosage as described in the invention: eczema has inflamed and swollen the skin tissue to a point that a lesion has formed with a crust forming around the edges of the lesion as the body is trying to repair the skin. The patient was then prescribed the liquid dosage as described in the invention at a dosage rate of 5 mls 3 times daily. The same flexural point one week after taking the liquid dosage as prescribed: inflammation and swelling previously present one week before has now diminished and the lesion is now healing over. The same flexural point two weeks after taking the liquid dosage as prescribed: the lesion has now completely healed, there is no longer any inflammation or swelling and the skin where the lesion had been is now clear of any eczema.

The condition of patient 2's upper arm, wrist and leg, respectively, before taking the liquid dosage as described in the invention: eczema has inflamed and swollen the skin tissue to a point that multiple lesions and spots have formed, this is particularly so at the flexural point. The patient was then prescribed the liquid dosage as described in the invention at a dosage rate of 5 mls 3 times daily. The same leg 6 days after taking the prescribed dosage as described in this invention: inflammation and swelling previously present has now decreased where the multiple lesions have started to heal over and have become superficial. The same upper arm and wrist area 27 days after taking the prescribed dosage as described in this invention: multiple lesions and spots have healed over leaving only the scar tissue from the eczema. The flexural point has healing scabs where previously there had multiple lesions, The condition of the wrists of patient 5 before taking the liquid dosage as described in this invention: eczema has caused multiple inflamed spots on the skin which have formed a crust over the areas of swelling. The patient was then prescribed the liquid dosage as described in the invention at a dosage rate of 5 mls, 3 times a day. The wrists of patient 5, 18 days after taking the dosage as described in this invention: skin where the eczema had affected has now completely cleared up of the eczema with the skin returning to a normal appearance, without any scars or presence of the customary spots of eczema, The condition of a flexural region on the elbow of patient 5 before taking the liquid dosage as described in this invention: eczema has caused inflamed spots and lesions to form along the creases of the flexural region. The patient was then prescribed the liquid dosage as described in the invention at a dosage rate of 5 mls, 3 times a day. The same flexural region after patient 5 has taken the prescribed dosage after 18 days: eczema has cleared up, the swelling and inflammation has disappeared and the skin has returned to a normal appearance.

The condition of the upper thigh of patient 7 before taking the liquid dosage as described in this invention: eczema has caused splotchy inflamed spots to appear on the skin. The patient was then prescribed the liquid dosage as described in the invention at a dosage rate of 5 mls, 3 times a day. The same upper thigh of patient 7 after taking the prescribed dosage for one week: eczema has almost disappeared with only a few spots remaining that are no longer inflamed.

The condition of patient 9's stomach area before taking the liquid dosage as described in this invention: eczema has caused patchy spots to appear all over the skin and unlike the previous figures, this eczema is not as inflamed or swollen. The patient was then prescribed the liquid dosage as described in the invention at a dosage rate of 7.5 mls, 3 times a day. The same stomach area 19 days after taking the liquid dosage as prescribed: the area is now clear of eczema with the skin starting to return to a smooth appearance, however the spots of eczema are still present.

The condition of patient 8's stomach area before taking the liquid dosage as described in this invention: eczema has caused inflamed red patchy spots to appear all over the skin. The body has been trying to heal the eczema and so there is also associated tan coloured patchy spots all over the skin as well. The patient was then prescribed the liquid dosage as described in the invention at a dosage rate of 5 mls, 3 times a day. The same stomach area 6 months after taking the liquid dosage as prescribed: eczema has now completely disappeared with the skin returning to a smooth blemish free appearance.

The condition of patient 10's arm before taking the capsule dosage as described in this invention: eczema has caused the skin to be scaly and dry with the associated inflammation and swelling of the skin in localised areas. The patient was then prescribed with the capsules of a dosage unit as described in this invention which were taken in groupings of 4 capsules, 3 times a day. The same arm almost 6 months after patient 10 has taken the capsule dosage as prescribed: skin is no longer dry and scaly. Rather the skin has a sheen that makes the skin appear as though the moisture has been replaced. The inflammation and swelling has decreased although it has not disappeared completely.

The condition of patient 4's wrist before taking the liquid dosage as described in this invention: eczema has caused inflammation and swelling of the skin along the flexural lines between the wrist and hand with small spots and lesions forming. The patient was then prescribed the liquid dosage as described in the invention at a dosage rate of 10 mls, 3 times a day. The same wrist 9 days after taking the prescribed dosage: the spots and inflammation have gone and the skin is returning to a smooth unblemished appearance. After about 2 weeks of taking the dosage, the skin is retaining the smooth unblemished appearance. After about 6 weeks of taking the dosage, there are now healing scabs along the flexural regions between the hand and wrist.

The condition of patient 4's flexural region on the arm before taking the liquid dosage as described in this invention: eczema has caused inflammation and swelling of the skin along the flexural lines with small spots forming. The patient was then prescribed the liquid dosage as described in the invention at a dosage rate of 10 mls, 3 times a day. The same flexural region 9 days after patient 4 has been taking the prescribed dosage: skin where the eczema had affected is now healing with the inflammation and redness disappearing. The skin is now returning to a smooth unblemished appearance.

The oral administration for the treatment of eczema and/or psoriasis can be in addition to any other medicament administered for such ailment whether administered orally, topically, parenterally, sublingually, etc.

In practice the present invention will involve ideally oral self administration of effective quantities of cetyl myristate alone or more preferably as a mixture of both cetyl myristate and cetyl palmitate.

Preferably in any such mixture the cetyl myristate comprises at least about half of the mixture or the serial application on a weight to weight basis. It is envisaged that daily doses will vary depending on patient needs and may range from 1 to 20 capsules per day. A capsule ideally contains between 5 to 370 mg of the mixture or cetyl myristate.

Trials with a variety of patients reliant upon dosage forms of cetyl myristate alone have shown favourable responses insofar as relief from the symptoms of IBS and/or IBD are concerned. It has been found however that enhanced benefits occur where there is at least a small proportion of cetyl palmitate in addition to the cetyl myristate and it is to the use of one such ratio of these active ingredients that the following trial examples relate.

Examples of use follows. Each briefly describes the patient's condition before and after the stated treatment using dosage forms (ie; "of the invention") each having about 350 mg of the mixture of cetyl myristate and cetyl palmitate. That mixture comprises by weight 95% cetyl myristate and 5% cetyl palmitate by weight manufactured by the process as disclosed in NZ Patent Specification No. 332959. In addition added excipients were present in the non gelatin two part capsule case.

TRIAL EXAMPLES

Patient 1 is Male and 5½ Years Old.

Has suffered since birth from eczema with associated intense pruritus generally all over the body. Patient 1 had multiple use of allopathic and homeopathic treatments including steroids and was on 11 different medications including Elocon, and a hydrocortisone cream.

At the first appointment, patient 1 was provided with the liquid form of a dosage unit as described in this invention which was taken at the rate of 5 mls 3 times a day.

Three weeks later, patient 1 showed marked improvement over the entire body and all itching and psoriasis had stopped.

At the conclusion of 6 weeks, the patient's skin was virtually normal and soft with all infected lesions totally healed.

Patient 1 maintains a daily dose of 5 mls 3 times a day and is now symptom and conventional medication free.

Patient 2 is Male and 3 Years Old.

Had eczema from head to toe with marked scratching apparent over the upper and lower limbs. The patient was unable to sleep due to the scratching and used a wide range of allopathic medical moisturisers and steroids to try and cure the eczema.

At the first appointment patient 2 was provided with the liquid form of a dosage unit as described in this invention which was taken at the rate of 5 mls 3 a day.

One month later, the itching was gone, patient 2 was sleeping through the night, and the skin was more normal although there was still some scratching evident.

Two months later as there had not been any more improvement the dose was increased to 10 mls 4 times a day. This resulted in a marked improvement all over the skin surface.

The patient's skin is now nearing normal and now uses only a mild emollient and Fucicort to treat local areas of infection in conjunction with the invention. No other medications are used.

Patient 3 is Female and 3 Years Old.

Had eczema over the legs, arms and abdomen with very rough, dry sand paper like skin. Patient 3 since birth had used bath oil and steroid creams to no avail.

At the first appointment patient 3 was provided with the liquid form of a dosage unit as described in this invention which was taken at the rate of 5 mls 3 times a day.

Two weeks later, the patient was seen again. There had been a marked improvement in the skin, especially in the extremity and abdomen regions. This dosage has now been reduced to 5 ml once daily.

The skin is continuing to soften and there is no longer any psoriasis. Patient 3 no longer takes any other medication or creams apart from the invention.

Patient 4 is Female and 6½ Years of Age.

This young girl has had chronic eczema since 18 months of age and has been associated with very dry cracking skin associated with intense psoriasis. Her mother has used extensive amounts of hydrocortisone, Elecon (another steroidal cream) and BK Lotion, all of which managed to contain the eczema in local patches. However, the skin has continued to be dry and itchy.

At the first appointment Patient 4 was provided with the liquid form of a dosage unit as described in this invention which was taken at a rate of 10 ml, 3 times a day. She was assessed in approximately one week and showed marked improvement, where her skin was less dry and the psoriasis or itch had improved.

Patient 4 continued with the invention over the next three months and continued improvement. Where her skin returned to normal with a lovely soft texture and the natural oils or sebaceous secretions were sufficient to moisturise her skin naturally. She has now used the medication for two years with no relapses.

Patient 5 is Female and 7 Years Old.

Had severe eczema at all flexural surfaces i.e knees, elbows, wrists and was on a medication of potent steroids including Dermol and Eumovate cream.

At the first appointment patient 5 was provided with the liquid form of a dosage unit as described in this invention which was taken at the rate of 10 mls 2 times a day which was mixed with honey.

Two and a half weeks later, the skin was beginning to return to normal on all flexural surfaces. This skin continued to improve and now patient 5 is symptom free and no longer taking the steroids. The patient has continued on with the invention.

Patient 6 is Male and 28 Years Old.

Had eczema over the entire body with associated intense psoriasis with roughened skin over the abdomen and back. He also suffered an intense itch at multiple small cracks in flexural regions of the body and was unable to participate in sport as the perspiration entering the cracks caused intense stinging and pain.

At the first appointment patient 6 was provided with capsules of a dosage unit as described in this invention which were taken in groupings of 4 capsules 3 times a day.

Three weeks later, the skin had improved in texture, the itching and the dryness had gone, and the number of cracks at the flexural areas had decreased.

The patient has suffered a relapse after 6 weeks; when the patient discontinued with the invention.

But upon resuming with the programme proscribed with the invention the patients skin returned to its former state and the patient now enjoys normal skin. He has been taking the invention for over a year now.

Patient 7 is Female and 3 Years of Age.

Patient 7 at age two was first seen with chronic eczema. Previous treatment included various bath oils, and a variety of hydrocortisone moisturising creams gave minimal improvement, and the eczema remained extensively all over her body.

Patient 7 was provided with the liquid form of a dosage unit as described in this invention which was taken at a rate of 5 ml, 3 times a day Patient 7 was reviewed after one week and showed a marked improvement. She has since continued with the invention and is on a maintenance dose of 5 ml once a day. She has used this medication over the last year, and has gone for periods of about six months without using the invention as described, however during the winter, she goes back on the invention again. She no longer takes any other medication.

Patient 8 is Male and 6 Months Old.

Patient 8 was seen first on 1 Nov. 2000 with a history of eczema since birth. The eczema covered his entire body, over arms, abdomen and face. The mother had been using various natural remedies and moisturising creams, such as Alpha Keri lotion and bath oils. However, he was very unsettled because of the psoriasis.

At the first appointment he was provided with the liquid form of a dosage unit as described in this invention which was taken at a rate of 5 ml 3 times a day. He was reviewed in one week's time where there was a marked improvement.

The skin on his abdomen, legs and face have now completely returned to normal. He now continues to do well on a maintenance dose of 5 ml, twice a day.

Patient 9 is Female and is 5 Years of Age.

Patient 9 has had eczema all her life. She does not get a full night's sleep because of the itch of psoriasis and has had recurrent infections. This has caused severe stress in her family. The mother had used all forms of steroid cream and had taken her daughter to naturopaths and homeopaths. All medications and portions prescribed did not alleviate the eczema and or psoriasis. This patient further has multiple allergies and is on a very strict diet. At the first appointment she was provided with the liquid form of a dosage unit as described in this invention which was taken at a rate of 7.5 ml, 3 times a day. She was reviewed in a week. There was some reduction in the psoriasis or itch, and the skin texture had improved slightly. The dosage was then increased to 10 ml, three times a day, and she was review in two weeks' time.

Her condition had improved sufficiently in that she was now getting a good night's sleep and her skin although improved in texture, had not got to a soft delicate feeling yet. However, due to the increase in sleep and less itching she was a much brighter, happier child.

Patient 10 is Female and 37 Years of Age.

Patient 10 has had severe chronic eczema involving her entire body, particularly her lower limbs. Patient 10 was only tried alternative medications including different supplements of Vitamin E, UPA oil and various lotions and lubricating creams to reduce the itch and problem with her skin.

At the first appointment Patient 10 was provided with capsules of a dosage unit as described in this invention which were taken in groupings of 4 capsules, 3 times daily. She has now been taking this dosage for approximately one year. She has reduced the dosage to 3 capsules, 3 times a day.

Patient 10 has lost all the itch and psoriasis that is associated with eczema and the texture in her skin, and particularly her lower legs have dramatically improved.

Patient 11 is Male and 41 Years of Age.

Patient 11 has severe chronic eczema associated with his face, arms, legs and abdomen. He was also very disturbed by the psoriasis or constant itch that was associated with his condition. He has been treated by dermatologists and has used high potency steroid creams, lubricating creams, including Aquacare and Lipobase.

At the first appointment Patient 11 was provided with capsules of a dosage unit as described in this invention which were taken in groupings of 4 capsules, 3 times daily.

He was assessed after one week where his psoriasis had now improved and he was able to sleeping through the night without having to scratch. He was assessed again after talking the prescribed dosage after a further 3 months and his skin has become soft and the psoriasis has completely cleared up.

He has discovered that if he stops taking the invention the rash and eczema return in approximately four days of stopping the treatment.

Improvement in overall skin condition is seen when a patient is prescribed the dosage unit as described in the invention. The intensity of the inflammation and the reduction in scaliness of the skin is reduced. Further the lesions produced by the eczema and psoriasis are reduced and the skin has virtually cleared up.

We claim:

1. A method of treatment of eczema in a mammal, comprising administering or having self-administered to said mammal an effective amount of a medicament consisting of cetyl palmitate and one or both of an excipient and a diluent, wherein said administration is oral administration.

2. The method of claim 1, wherein said mammal is a human being suffering from eczema.

3. The method of claim 1, wherein said medicament is a capsule.

4. The method of claim 1, wherein said cetyl palmitate is present in a dosage unit containing between 0.1 to 200 mg cetyl palmitate.

5. A method of treatment of eczema in a mammal, comprising administering or having self-administered to said mammal an effective amount of a medicament for relief of a symptom of eczema, wherein said medicament consists of cetyl palmitate and one or both of an excipient and a diluent.

6. The method of claim 5, wherein said mammal is a human being suffering from eczema.

7. The method of claim 5, wherein said medicament is a capsule.

8. The method of claim 5, wherein said cetyl palmitate is present in a dosage unit containing between 0.1 to 200 mg cetyl palmitate.

* * * * *